United States Patent [19]
Geho et al.

[11] Patent Number: 4,603,044
[45] Date of Patent: Jul. 29, 1986

[54] HEPATOCYTE DIRECTED VESICLE DELIVERY SYSTEM

[75] Inventors: W. Blair Geho; John R. Lau, both of Wooster, Ohio

[73] Assignee: Technology Unlimited, Inc., Wooster, Ohio

[21] Appl. No.: 606,714

[22] Filed: May 3, 1984

Related U.S. Application Data

[63] Continuation-in-part of Ser. No. 456,270, Jan. 6, 1983, abandoned.

[51] Int. Cl.⁴ ............................................... A61K 49/00
[52] U.S. Cl. ........................................ 424/9; 436/829; 428/402.2; 424/38; 514/3
[58] Field of Search ...................... 428/402.2; 424/178, 424/38, 9, 1.1; 436/829

[56] References Cited

U.S. PATENT DOCUMENTS

| | | | |
|---|---|---|---|
| 4,091,088 | 5/1978 | Hunt et al. | 424/9 |
| 4,310,505 | 1/1982 | Baldeschwieler et al. | 428/402.2 |
| 4,318,898 | 3/1982 | Molter et al. | 424/9 |
| 4,377,567 | 3/1983 | Geho | 428/402.2 |

FOREIGN PATENT DOCUMENTS 1545427  5/1979  United Kingdom .

Primary Examiner—Richard D. Lovering
Assistant Examiner—Anne Brookes
Attorney, Agent, or Firm—Frijouf, Rust & Pyle

[57] ABSTRACT

A targeted drug delivery system which has specificity for hepatobiliary receptors, which are the specialized metabolic cells of the liver. Hereinafter, this will be referred to as a Hepatocyte Directed Vesicle, or abbreviated as HDV. This preferred directed delivery system utilizes a bipolar lipid for the majority of its vesicle membrane structure.

The targeting material, which is only a minor constituent of a targeted vesicle system, has a specificity for hepatobiliary receptors of the liver. The Hepatocyte Directed Vesicle is then attracted to the receptor, and the vesicle releases its pharmacological cargo.

This disclosure specifies that the attachment of the targeting material, or molecule, to the vesicle is preferably done by first providing a connector molecule, having a portion inserted into the wall of the vesicle, by reason of being lipophilic, and a portion which is hydrophilic and is projected from the vesicle wall.

The target, by connector molecules, are tied together to extend or project the target molecule a distance from the vescile wall.

Any chemical molecule capable of circulating in the bloodstream of a warm-blooded animal and attracted to the hepatobiliary receptors will serve as a target substance for this invention.

This invention is in the discovery of a unique and unprecedented result of directing a vesicle containing a pharmacological load to the hepatobiliary receptors.

7 Claims, 6 Drawing Figures

HEPATOCYTE DIRECTED VESICLE DELIVERY SYSTEM

CROSS-REFERENCE TO RELATED APPLICATIONS

This application is a continuation-in-part of U.S. application Ser. No. 456,270, filed Jan. 6, 1983, now abandoned, which was copending with application Ser. No. 75,310, filed Sept. 13, 1979, now U.S. Pat. No. 4,377,567.

BACKGROUND OF THE INVENTION

1. Field of the Invention

This invention is a chemically structured delivery system for targeting drugs, hormones, biologicals or diagnostic materials to the hepatocyte.

2. Description of the Prior Art

Applicant's prior U.S. Pat. No. 4,377,567 is a disclosure of the use of digalactosyl diglyceride to target vesicles containing drugs, hormones or other biological and diagnostic materials to the liver. For a full development of the prior art, the disclosure of that prior patent is referred to and incorporated by reference.

Hunt U.S. Pat. No. 4,091,088 assesses the hepatobiliary function by a reagent which is labelled with technetium 0.99 m for use as a hepatobiliary imaging radiopharmaceutical. This material does not affect the liver other than to provide scanning capability for diagnoses.

Molter U.S. Pat. Nos. 4,318,898 and 4,350,674 also assess the hepatobiliary receptors and caused a quick passage to the biliary system for diagnostic, not treatment, function.

Great Britain Pat. No. 1,545,427, issued in 1979, also uses the hepatobiliary system to diagnose the biliary system.

Applicant distinguishes over this and all known prior art, including intensive literature studies, by the discovery that:

(a) the hepatobiliary receptor targeted vesicle will not be merely passed to the biliary system, as would be expected from prior art teaching.

(b) the hepatocyte directed vesicle system targeted to the hepatobiliary receptors of the hepatocytes will be utilized to deliver hormones and drugs to the liver.

SUMMARY OF THE INVENTION

This invention resides primarily in the discovery that a bipolar lipid vesicle containing a pharmaceutical load can be directed to the hepatobiliary receptors of a liver. It has been discovered that instead of passing through to the biliary system as expected, a vesicle directed to the hepatobiliary receptors will be retained by the hepatocyte with exceptional efficiency.

With that discovery in place, it is then the function of this invention to successfully and properly construct a hepatocyte directed vesicle (HDV) which is directed to the hepatobiliary receptors.

It is, therefore, an object of the invention to enhance the efficiency of hepatocyte directed vesicles in general, by projection of the target molecule away from the surface of the vesicle.

Another object of the invention is to enhance the efficiency of liver medication by accessing the hepatobiliary receptors of the liver.

Yet another object of the invention is to provide a hepatocyte delivery system comprising a composite of a vesicle and a hepatobiliary targeting molecular wherein the vesicle's pharmacologic cargo is detached from its targeting system and retained by the liver cell where it can carry out its pharmacologic action.

The outstanding object of the invention is implementation of the discovery that the hepatocyte delivery vesicle can be directed to the hepatobiliary receptors of the hepatocyte, and not merely pass through to the biliary system, but the pharmacological cargo is retained by the hepatocytes of the liver, and enabled to carry out its pharmacologic action.

Another object of the invention is to prevent contact of the pharmacologic cargo with cells and tissues of the body which are not intended target tissues, thereby enhancing the specificity and potency of the pharmacologic cargo, and reducing its nonspecific toxicity.

Another object of the invention is to enable the use of the HDV by intraduodenal (oral), intravenous, subcutaneous and intramuscular routes of administration.

DETAILED DESCRIPTION

The present invention relates to compositions and processes for delivering pharmacologically-active agents preferentially to heptatocytes of the liver. The liver is composed of two types of cells: hepatocytes or metabolic cells, and reticuloendothelial cells (RE cells) which are scavenger cells. More specifically, this invention provides Lipid Membrane Structures (vesicles, liposomes) directed by hepatocyte target molecules and coupling of molecules to the lipid membrane of the vesicle to carry drug agents such as insulin preferentially to the hepatobiliary receptors of the hepatocytes, but not the RE cells.

This invention has generally application for improving the efficiency of accessing the hepatocyte because of the extension of the target molecule away from the surface of the vesicle. However, the primary function of the preferred embodiment, which is detailed herein, is to access the hepatocyte by utilizing the hepatobiliary receptors of the hepatocyte cell surface. The hepatobiliary receptors are known to receive substances for the liver intended to be delivered as bile to the biliary system, whereas liver (hepatocyte) treatment with liposomes has generally been accomplished by accessing the Ashwell receptors of hepatocytes by galactosyl targeting molecules.

The liver is the human body's largest gland and, as such, receives a massive blood supply through both the portal vein and hepatic artery. Metabolically, the liver is the most complex organ in the human body and, among other multiple functions, it metabolizes/distributes drugs which are introduced into the organism. The liver is also a target organ for pharmacologically-active agents produced within the body. Accordingly, an improved means for preferentially delivering drugs to the liver provides a means for allowing the drug to be handled by the body in a more natural fashion, thereby improving drug therapy.

The means whereby the liver handles insulin illustrates the activity of this important target organ.

Insulin is a hormone which affects the metabolism of the animal as a whole. The most dramatic effect of this hormone is its ability to reduce the concentration of glucose in plasma. Ingested carbohydrate meals are normally digested to glucose in the gut and then absorbed in the portal circulation. The pancreas responds to carbohydrate in the gut with a release of insulin into the portal circulation. The portal vein carries the absorbed glucose and the released insulin to the liver. At the liver the insulin regulates the metabolism of glucose by the heptatocytes. By an unknown mechanism the liver retains most of the insulin but releases some to facilitate glucose utilization by muscle and adipose tissue. Reduction in blood glucose is due to the insulin effect on both liver and peripheral tissues. Thus, while the pancreas is the source of insulin within the organism, the liver is the key to its normal utilization.

Insulin therapy for diabetes mellitus began in 1922. In current medical practice insulin is administered subcutaneously because the oral administration of the insulin is inefficient, presumably due to proteolysis. Subcutaneously administered insulin does produce a lowered level of blood glucose, primarily as a result of its action on muscle and fat tissue. However, insulin administration by injection can hardly be classified as a near normal state. Importantly, the anatomic arrangement of the pancreas in the normal individual is such that high levels of insulin secreted by the pancreas in response to oral glucose loads pass by way of the portal circulation to the liver before entering the peripheral circulation. By comparison, when insulin is administered subcutaneously to the diabetic patient, the peripheral tissue has first access to the hormone and may reduce the level of insulin presented to the liver and, in turn, reduces the effectiveness of the liver as a significant glucose regulating mechanism. Therefore, insulin administered by injection does not have the same physiological action as insulin released from the pancreas.

The present invention provides an improved means whereby insulin or other pharmacologically-active agents can be delivered preferentially to the liver in a human or lower animal.

The Lipid Membrane Structures used herein comprise a bipolar lipid and a target molecule conjugate.

The preferred polar lipid used in the practice of this invention is distearoyl lecithin. Natural lecithin (phosphatidyl choline; vitellin) comprises a mixture of the diglycerides of stearic, palmitic and oleic acids linked to the choline ester of phosphoric acid and is found in all living plants and animals. Vesicles from such polar lipids are known art.

The term "liposome" is generally referred to by the term "vesicle", but both are interchangeable for the purposes of this disclosure. The vesicle may be unilammelar or multilamellar and range in size from 250° A to 5 microns in diameter.

The HDV is useful in delivering drugs, hormones, biologicals or diagnostic materials to the liver. The liver is a difficult organ to reach with exogenously administered drugs, and the HDV presents a unique therapeutic advance, making it possible to deliver drugs, hormones, biologicals and diagnostic materials in a more efficient, safer way than those means currently available. The reason for the "therapeutic unavailability" of the liver to conventional therapies is that the liver is anatomically situated in such a way that it is isolated from the rest of the body with respect to its blood circulation. The majority of the liver's blood comes to it by way of the portal circulatory system which is a highly localized, low-pressure, venous system designed to carry absorbed nutrients (products of digestion) from the intestines to the liver for metabolism. The arterial blood supply takes care of the rest of the body before a small portion of it reaches the liver via the portal system.

In view of the fact that the liver is a difficult organ to reach with exogenously administered drugs, this invention provides a biological carrier system that utilizes hollow bipolar liposomes in conjunction with a family of liver molecules to effect delivery of the prescribed drug.

The following diagram schematically sets forth the basic structure of a functional HDV:

The following structure depicts the basic liposome or bipolar lipid vesicle:

Where —o is a polar lipid, and the — represents a lipophilic portion, and the o represents the hydrophilic portion.

The vesicle is a sphere with an aqueous core, where the sphere is a bipolar lipid membrane with hydrophilic surfaces and a lipophilic (hydrophobic) interior of the membrane. The aqueous core can contain water-soluble substances such as drugs, hormones, minerals, diagnostic agents, and biologicals. Lipophilic substances are not carried in the core volume but in the bipolar lipid membranes.

The targeting mechanisms require that the molecular target molecule be positioned on the surface of the liposome or vesicle in such a manner that the target molecules are available for interaction with its intended receptor molecule which is on the surface of the intended cell. The target molecule is positioned so that it is extended away from the membrane surface. See the illustration above for a pictorial representation.

The HDV is fashioned in such a way that a connector portion is first incorporated into the membrane at the time of forming the membrane. The connector portion must have a lipophilic portion which is firmly embedded and anchored in the membrane. It must also have a hydrophilic portion which is chemically available on the aqueous surface of the vesicle. The hydrophilic portion is selected so that it will be chemically suitable to form a stable chemical bond with the target molecule which is added later. Therefore, the connector molecule must have both a lipophilic anchor and a hydrophilic reactive group suitable for reacting with the target molecule and holding the target molecule in its correct position, extended out from the vesicle's surface. In some cases it is possible to attach the target molecule to the connector molecule directly, but in most instances it is more suitable to use a third molecule to act as a chemical bridge, thus linking the connector molecule which is in the membrane with the target molecule which is extended, three dimensionally, off of the vesicle surface.

An important aspect of this invention is the fact that the target molecule can be any molecule that is recognizable by the hepatobiliary receptors of the hepatocyte. The term "hepatobiliary" is defined in the 1965 edition of *Dorland's Illustrated Medical Dictionary*, W. B. Saunders and Company, Philadelphia, as "pertaining to the liver and the bile or biliary ducts." The hepatobiliary receptors of hepatocytes are capable of recognizing and of taking into the hepatocyte a great variety of chemical structure. The nature of the target molecule is therefore most clearly defined by its biological specificity for the hepatobiliary receptors of hepatocytes.

DEFINITION

This invention therefore can use as a target molecule, any chemical substance which can be taken into the hepatocytes and transported into the biliary system. Because of this diversity it is necessary to have this biological definition of the target molecule rather than a chemical definition.

EXAMPLES

A variety of chemical structures are shown below which are chemically diverse but are generally recognized as hepatobiliary chemicals and act as effective hepatocyte target molecules. Because of the variety of chemicals that can be used by this invention as target molecules, it is necessary to provide an appropriate variety of chemical means to attach these molecules to the surface of the vesicle. This variety therefore requires a number of different connectors and chemical bridge systems to permit the use of this variety of chemical structures commonly referred to as hepatobiliary materials.

While the majority of hepatobiliary target materials will require the techniques of attachment generally described above, some will be suitable for use as a single molecule because they will have a chemical portion that acts as "connectors" and other portions that act as "target molecules." Examples of useable systems will therefore include representative of both the multiple step (connector-bridge-target) system, and the single step system just described.

The structural formula below is an example of the result of a multiple step method of constructing a Hepatocyte Directed Vesicle (referred to as HDV).

Connector molecule | Bridge | Target molecule

In the structure above a series of lines and small circles symbolize the positioning of bipolar lipid membranes which encircle a vesicle core volume. This structural representation is grossly out of proportion for convenience of illustration. The bipolar vesicle is actually huge in comparison to the connector-target molecule.

Under the bracket labelled "connector molecule" is an iminodicarboxylic acid molecule having a lipophilic and a hydrophilic end. The lipophilic end is the end containing the benzene ring and is shown embedded into the bipolar film of the vesicle.

The hydrophilic portion of the connector molecule will extend away from the fact of the vesicle because it is water loving.

Under the bracket labeled "target molecule" is, in this particular illustration, an identical iminodicarboxylic acid as that in the connection molecule. This is one acceptable, and perhaps preferred embodiment, but by no means is it an exclusive requirement. That is, the connector and target molecules are illustrated as being identical in this embodiment, but that is not a requirement. It is a requirement of this preferred embodiment that the target molecule be a molecule which is recognized by the hepatobiliary receptors of the liver as opposed to sugar-type molecules which are normally attracted to the Ashwell receptors.

Under the bracket labeled "bridging ion" is a chromium bridge which will connect the hydrophilic charged terminal ends of the two iminodicarboxylic acid groups. These groups would not normally connect to one another; therefore, the chromium ion is used for that purpose. There are other possibilities wherein a hepatobiliary target molecule may be directly connected to a connector molecule.

The hepatobiliary targeting molecule may be employed to bring a vesicle into that portion of the liver which normally is concerned only with creating bile fluids. After this discovery, a wide range of possible combinations of connectors and target molecules may be visualized. It is therefore only up to the innovative chemist to select from the great number of possible combinations to achieve the necessary results.

It is not obvious that the hepatobiliary receptors will accept a system which includes a vesicle and drop off the vesicle in the hepatocyte where it releases its pharmacologic cargo and is effective, with the remainder of the system passing onto the bile duct just as would be expected of anything taken into the hepatobiliary receptors.

In the study and experiments done to validate this invention, it appears that much larger and greater number of vesicles may be taken into the hepatocyte through the hepatobiliary receptors.

I. Chemistry

A. Preferred bulk bipolar lipid constituents (75%–95%)
   1. Distearoyl lecithin (DSL)
   2. Dipalmatoyl lecithin (DPL)
   3. Other lecithins with chain lengths C10–C20
B. Minor constituents (0.1–25%) for stability
   1. Cholesterol
   2. Dicetyl Phosphate
   3. Albumin
C. Target Molecules (0.1%–10%)
   Hepatocyte specificity is conveyed by molecules having the following structure which have both hydrophilic and hydrophobic portions:

_Preferred Target Structure #1_

(benzene ring with $R_1$, $R_{2a}$, $R_{2a}$ substituents)

\\ Hydrophilic /   \\ Hydrophobic /

This portion is responsible for targeting

_Preferred Target Structure #2_

(benzene ring with $R_1$ and $R_{2b}$ substituents)

\\ Hydrophilic /   \\ Hydrophobic Targeting Portion /

Where
$R_1$ has the following structure(s) and n = 1–3, $$[-O-\overset{O}{\underset{\|}{C}}-(CH_2)_n]_2-N-CH_2-\overset{O}{\underset{\|}{C}}-\overset{H}{\underset{|}{N}}-$$

$R_{2a}$ has the following structure(s):

(1)$CH_3$, (2)$CH_2CH_3$, and (3)$CH(CH_3)_2$ $R_{2b}$ has the following structure:

$CH(C_3)_2$

_Preferred Target Structure #3_

N-(3 Bromo-2,4,6-trimethylphenyl carbamoyl methyl)imino diacetic acid

_Preferred Target Structure #4_

N-(3-Cyano-4,5-dimethyl-2-pyrrl carbamoyl methyl)imino diacetic acid

_Preferred Target Structure #5_

D. Biliverdin (or Bilirubin) Preferred Bridge Examples
   1. Inorganic salts of:
      a. Chromium
      b. Cobalt
      c. Iron
      d. Zinc
   2. Organic
      a. Ethylene Diamine
      b. Propylene Diamine
   Connectors With each of the preferred target structures, the preferred connector is the same as the target. The preference is only for the convenience of the manufacturer.

It should be noted that in the target structures the diacetic acid portion provides oxygen bonds for connecting through a bridge to a connector molecule presenting similar oxygen bonding points. The bridge molecules provide the necessary ligands to connect to each of the four oxygens and thereby interconnect the target and connector molecules.

Although the foregoing is preferred, it is not essential that identical molecules be used for connector and target with a bridge interconnection. An example of an alternate connector means not using a bridge is to incorporate albumin into the vesicle membrane then react the proprionyl group of bilirubin as a target with a lysine amino group to form a Schiff base. In this example, no bridge molecule is used per se.

Therefore, it is within the penumbra of this invention to form a single-step target system without separate connector and bridge molecules.

These examples are of materials that are incorporated into the HDV in one step, not requiring the multiple step addition of bridge and then target molecule, although portions of the large molecule conjugates can be designated as "connector", "bridge" and "target".

There are four parts to the completed preferred HDV:
   1. Vesicle, which carries the cargo
   2. Vesicle connector molecule
   3. Bridging molecule
   4. Target molecule In this invention the connector molecules and the target molecules can be identical. That is to say that two identical molecules which are connected by a specific molecular bridge, when appropriately attached to the vesicle surface, form the completed HDV system.

However, it is also possible to connect two dissimilar molecules by a bridge, thereby enabling selection of various useful combinations of target and connector molecules which would not otherwise be compatible. This is within the skill of the biochemist after the concepts of the invention have been understood.

In the preferred target structures above for the hepatobiliary receptors where $R_1$ has the preferred structure of n = 1 in order to maximize the negative charge on the carboxyls, n may be extended with additional methylenic ($CH_2$) groups with concomitant reduction of the negative charge on the carboxyl group, which would result in a progressively weaker ligand connecting the bridge.

PREPARATION OF THE PREFERRED EMBODIMENT

This development describes the coupling of a liver targeting agent to a vesicle membrane for the purpose of creating a new targeting system. There is an orderly sequence of events that is required for the successful coupling of the targeting agent to the vesicle membrane. The preparation of the vesicle targeting system initially requires the formation of a vesicle structure with a connector molecule embedded into the membrane. In the course of this development there have been two special ligands utilized to attach the connector molecules to the targeting molecules. Initially, an inorganic substance, chromium chloride, was used. Concern about long-term chromium toxicity arising from continual vesicle dosing has been dispelled by further study, but organic ligands such as $H_2N-CH_2-(CH_2)_n-NH_2$ where $n = 1-4$, (i.e. ethylene diamine) is an alternative for coupling purposes. However, from a practical point of view, both ligands serve the same function.

Described below is a reaction sequence relating the various steps involved in the formation of an HDV system. Each step is unique in relation to the next step and each subsequent step in the reaction sequence. This is the preferred embodiment.

The first step of the sequence requires that the connector molecule and the lipid components comprising L-α-distearoyl lecithin (DSL), dicetyl phosphate (DCP) and cholesterol (CHOL) in conjunction with human serum albumin (HSA) be formulated into a vesicle structure with a bipolar membrane.

As a result, the connector molecule is oriented in three-dimensional space as noted above. This three-dimensional position of the connector molecule creates the foundation for the successive reactions resulting in the structures completing the HDV. At this step the entire vesicle is acting as a large suspended structure with the vesicle surface interspersed by a uniform distribution of connector molecules, three-dimensionally poised to partake in the next reaction sequence. The hydrophilic portion of the connector molecule projects into the aqueous phase of the media, whereas the hydrophobic portion of the molecule is buried in the lipophilic section of the membrane. Since the molecular size of the connector molecule is small in comparison to that of a vesicle and since only a portion of the connector molecule is entrapped in the vesicle structure at the time of preparation, the remaining unentrapped connector molecules can be removed easily by Sephadex G-100-120 gel filtration chromatography.

In the next step a five-fold molar excess with respect to the initial concentration of connector molecules, of either $CrCl_3$ hexahydrate or ethylene diamine (which are examples of bridging molecules) is reacted with the vesicle structure containing the embedded connector molecule to form a vesicle connector molecule-bridging molecule complex. As a result of this step, the proper three-dimensional orientation of the bridge molecule is established for the subsequent binding of a targeting molecule to the vesicle-connector molecule-bridging molecule complex.

In the final step the the target molecules are added to the vesicle-connector-bridge complex. A five-fold molar excess of target molecules is reacted with the vesicle structure containing the vesicle connector molecule-bridging molecule complex to form the vesicle connector molecule-bridging molecule-target molecule conjugate to be used for vesicle targeting purposes. The excess unreacted target molecule may then be removed by Sephadex G-100-120 gel filtration chromatography.

In summary, the unique steric symmetry and structure of the targeting molecule permits it to be functional and useful in its targeting role. This unique, three-dimensional symmetry can be achieved through utilizing the reaction sequences as described in the aforementioned paragraphs.

The new chemistry featured in this targeting system is that a molecule that is both hydrophilic and hydrophobic can be converted to a hydrophobic targeting moiety with the concommitant neutralization of the charged portion of the molecule through ligand formation and, in addition, provide the correct three-dimensional orientation or projection of its hydrophobic targeting portion into the hydrophilic aqueous media.

Thus, the sequence in which these molecules are reacted promotes and establishes the proper orientation of the insoluble hydrophobic group in spite of the unfriendly environment posed by the aqueous media toward hydrocarbon structures.

Furthermore, the negative charge contributed by dicetyl phosphate (one of the membrane constituents) at the surface of the vesicle, creates charge-charge repulsion between vesicles and facilitates their suspension and shelf-life stability. The negatively charged phosphate at the hydrophilic end of the molecule at neutral pH is responsible for the charge-charge repulsion effect resulting in vesicle stabilization.

This charge-charge repulsion is strong enough (probably by two-orders of magnitude) to overcome any van der Walls induced dipole interactions caused by the hydrophobic phenyl ring and the accompanying R-groups.

Method for Preparing HDV

DSL—69.12 mg, —iminodiacetic acid complex 1.07 mg, DCP—14.1 mg, CHOL—5.0 mg 1.5 ml of $CHCl_3$.MeOH (2:1 v/v) was added to solubilize the reagents. The sample was placed on the rotoevaporator and taken to dryness at 60° C.±0.5° C. with slow turning under aspirator vacuum. Then 2.4 ml of freshly prepared 40 mM phosphate buffer pH 7.4 with a concentration of HSA and serotonin, the active agent at 4.2 mg/ml and 10 mg/ml, respectively, were added to the dried lipid components. The sample was sonicated using a Heat Systems Ultrasonic Cell Disruptor at setting #4 equipped with a transducer and cup horn at 60° C.±0.5° C. for 15 minutes. Next, the sample was annealed at 60° C.±0.05° C. with slow turning for 15 minutes. Then the sample was centrifuged in a Triac Clinical Centrifuge at the blood setting for 15 minutes at room temperature.

Then, 1.5 ml of the supernatant was chromatographed on a 1.5×25.0 cm Sephadex G-100-120 column that had been previously equilibrated with 40 mM phosphate buffer pH 7.4. This first chromatography was performed in order to remove the unentrapped HSA and serotonin, the active agent. The lipid vesicles were collected and then, with respect to the initial concentration of vesicle connector molecules, were reacted with a five-fold molar excess of $CrCl_3$. The vesicles were then rechromatographed using the same buffer to remove unreacted $CrCl_3$. The collected vesicles were then reacted with a five-fold molar excess of connector molecules. Following this step the vesicles were then rechromatographed using the same buffer system to remove unreacted connector molecules. Following this final chromatography, the vesicles were stored under nitrogen in the refrigerator at 5° C. Phenyl-mercuric nitrate may be used as a preservative (0.001%).

In Vivo Testing of the Preferred Embodiment

To test the invention an in vivo model is used. It must be borne in mind that the test is for successful delivery of a pharmaceutical dose to the liver. The delivery of the cargo is established by demonstrating the desired pharmacological response to the cargo by the liver.

The entire thrust of this invention, hence the disclosure of the many preferred approach methods, is to establish factually by in vivo testing that the pharmaceutical load carried within a vesicle can and is delivered to the liver of a warm-blooded animal and that the pharmacologic cargo is made available to act at the hepatocyte. In order for the pharmacologic cargo to act on its receptor, the HDV must be effectively dismantled, releasing the cargo from the protective coating of the vesicle. The pharmacologic cargo may then be used by the liver to cause a hormonal control of the liver as in the natural functioning state of healthy individuals.

This inventor has also discovered and established beyond doubt that the liver storage of glucose eaten during a meal requires not only the hormone insulin, but also that a co-factor is required for proper liver function. That co-factor is serotonin. Serotonin is a chemical, 5-hydroxytryptamine (5-HT), present in platelets, gastrointestinal mucosa, mast cells, and in carcinoid tumors. Serotonin is a potent vasoconstrictor (Taber's Cyclopedic Medical Dictionary, 14th Edition). This inventor has established that Serotonin is supplied to the portal vein leading to the liver while food is being absorbed by the intestines and is controlled by the central nervous system. Thus, it was discovered that by severing the vagus nerve the serotonin in the portal vein could be essentially eliminated. When this is done, it is now established, the liver no longer will convert the nutrient glucose to glycogen and store the glycogen. Rather, the liver will allow all of the glucose to proceed into the peripheral system, thereby producing excess sugar in the blood and providing the symptoms of diabetes. Although there may be sufficient insulin available at all times at the liver, a deficiency of serotonin will result in an excess of glucose in the blood.

By providing a serotonin load in this hepatocyte delivery vesicle and targeting the vesicle to the hepatobiliary receptors of the liver, and observing the return to normal liver function, this inventor has clearly established the ability of the target vesicle system of this invention to effectively deliver a pharmaceutical load to the liver, whatever the load may be. If diagnostic material is desired, or insulin, or as in the case of hypoglycemia, the blocking agents for the serotonin function, the unique capability of this invention has been established.

Hence, in a dog model having a normal insulin production by the pancreas glands, it is a superior test of the HDV to denervate the glands producing serotonin, and after establishing diabetes symptoms of excess blood glucose, to direct serotonin (5HT) to the liver. Re-establishment of normal liver glucose control then proves effective HDV delivery to the hepatocyte.

In a first study testing the HDV system, a chronic dog model was selected which mimics the early stages of adult onset diabetes mellitus, now referred to as diabetes mellitus Type II. In this model, the diabetes was induced by selective denervation. The normal healthy dogs prior to denervation respond to a standard meal (one-third carbohydrate) by having slightly lowered levels of peripheral blood glucose. Following denervation, the dogs maintain normal fasting blood glucose values, but their peripheral blood glucose levels rise significantly after a standardized meal, thus responding in a similar manner to adult onset diabetes.

This particular model was selected for this study because it enabled the evaluation of the HDV system in alert, unanesthesized animals.

This study was divided into three phases, studying the blood glucose response of the animals while in the (1) normal state; (2) diabetic-like state; and (3) successful treatment of the diabetic-like state with subcutaneously administered HDV containing serotonin.

The experimental plan required four normal, healthy mongrel dogs. This first phase of the study was to determine the blood glucose response of these four dogs to a standardized glucose meal, comparable to the oral glucose tolerance test in people. The graph of FIG. 1 is a comparison chart for in vivo testing.

The data for this normal phase are shown in the graph as the line indicated by reference number 10. The data are expressed as a percentage of the fasting blood glucose value taken prior to feeding. Since four dogs were used, the average or mean value for the data is plotted. The data are statistically analyzed, and the variation in the data is shown by the small vertical bars above and below the data points. These bars are the standard error of the mean (SEM).

Following the acquisition of the data described above, the dogs were surgically denervated to induce the diabetic-like state and allowed a week to recover. At this time the study is again repeated, and the data are shown as the line indicated by reference number 12, along with the error bars (SEM). It is clearly seen from the data that the animals' responses were different following the denervation. The asterisks (*) at the 1, 2, 3 and 4 hour data points along the line 10 indicate that by statistical analysis of the data by the conventional student's t test, the blood glucose response of the dogs following surgery is statistically different from the response of the dogs prior to surgery. The level of significance is less than 5% (designated, therefore, as $p<0.05$). This means that there is less than a 5% chance that the difference observed would have happened randomly.

The third phase of the study was to repeat the standardized meal in the diabetic-like dogs, but with the dogs injected subcutaneously with 1.0 ml of HDV-containing serotonin. The total dose of serotonin in the HDV was 150 ug serotonin, and it was administered one hour prior to eating and immediately after taking the baseline blood glucose sample. The response of the HDV-serotonin-treated denervated dogs is shown in line 14. The abnormal elevation of the blood glucose has been normalized. At one, two and four hours the data points were $p<0.06$, $p<0.05$ and $p<0.05$ for this treatment, compared to the post-denervation meal 12.

The data from these studies are summarized in the bar graph of FIG. 2.

The first bar shows that the average value for the blood glucose (hours 1–4) for the dogs prior to surgery decreased about 10% after a meal compared to their blood glucose value taken prior to eating. In the second bar, the mean blood glucose response (hours 1–4) was increased after a meal, and the asterisk indicates that it was statistically significant ($p<0.01$, student's t test). The denervation had caused an elevation in blood glucose following a meal, thus inducing a diabetes-like state. The third bar shows the effect of the HDV-serotonin treatment. The HDV serotonin significantly decreased the elevation of the blood glucose following a meal.

It is most important to know that in studies by the inventor it has been established that serotonin administered at this dose (150 ug) is not effective either intravenously or subcutaneously in inducing the effect seen with the HDV-serotonin in these studies.

The conclusions from these data are:
1. Denervation produced a diabetic-like state.
2. The effects of denervation could be corrected with very low doses of HDV containing 5-HT.

Figure 1:
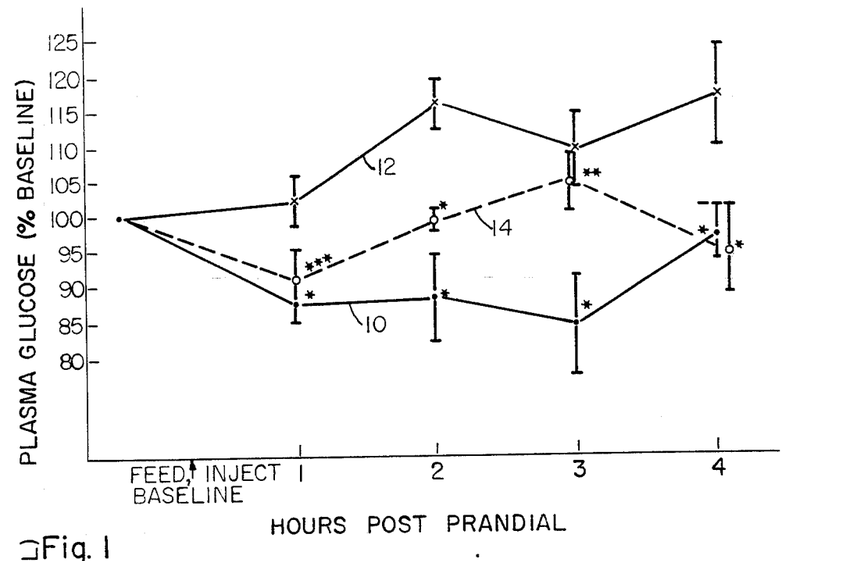
FIG. 1 is a graph depicting the plasma glucose levels of normal dog models which were denervated, tested for diabetes, and then normalized by this invention.
Figure 2:
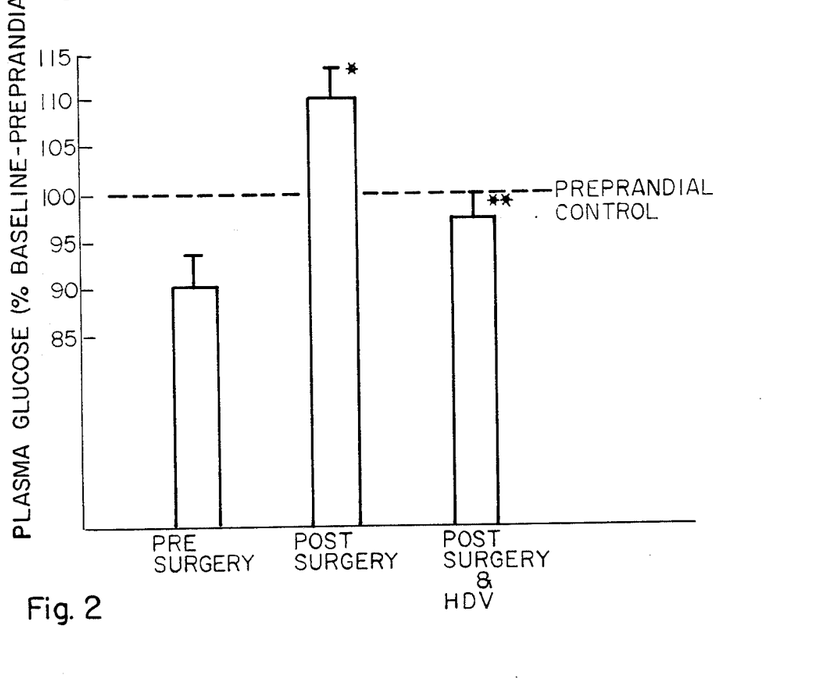
FIG. 2 is a bar graph summarizing the data of FIG. 1.
Figure 3:
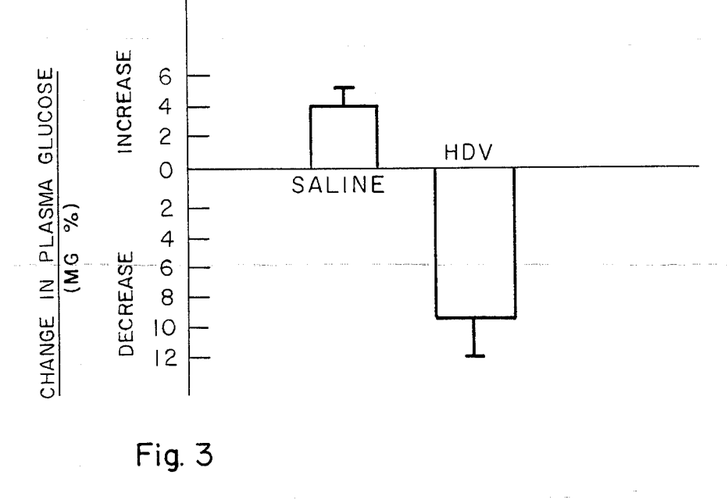
FIG. 3 is a graph of blood sugar level after a controlled dose of saline on a diabetic fasting dog, and compared result after administering HDVS.
Figure 4:
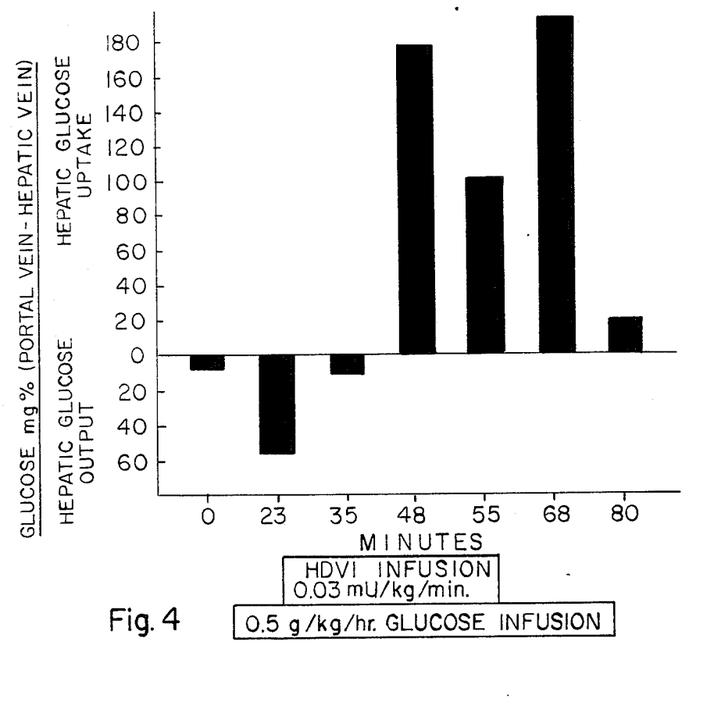
FIG. 4 is a graph showing the change from glucose output to uptake following infusion of HDVI.
Figure 5:
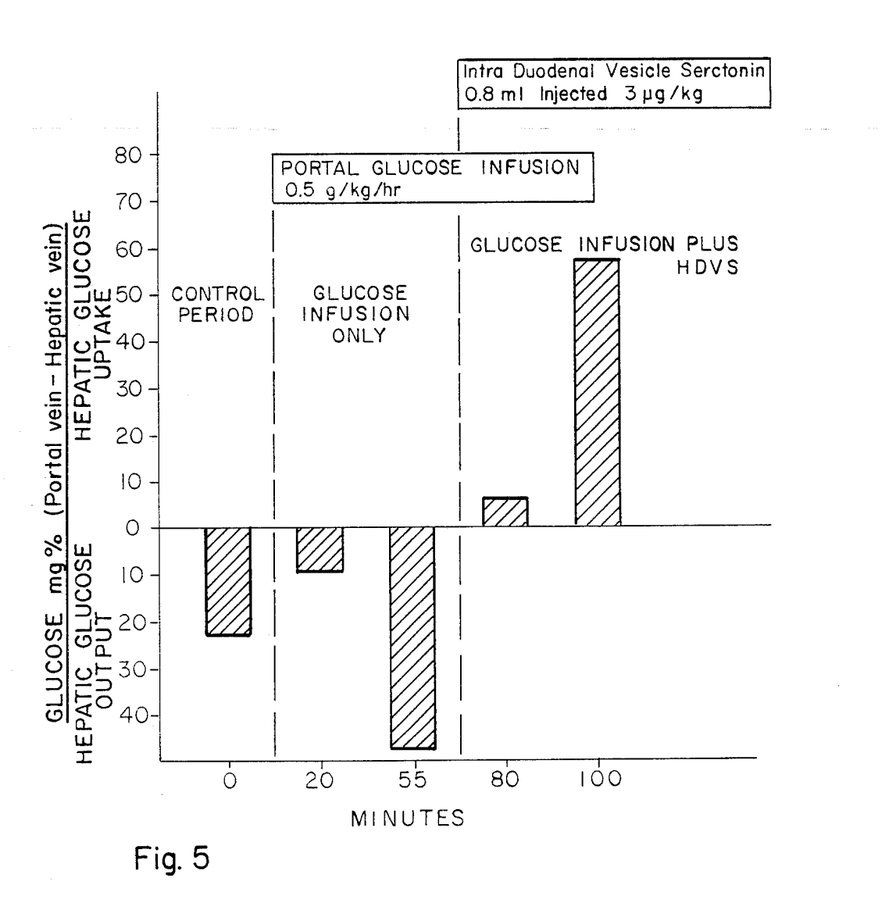
FIG. 5 is a graph comparison of the effect of correcting the lack of control serotonine on diabetic animals via an oral dose.

A second study tested the hypoglycemic (blood glucose-lowering ability) effectiveness of HDV containing 5-HT in fasting (non-fed) dogs. The graph of FIG. 3 summarizes the results. Four dogs (denervated as in the first study) were used in the study on two different days. The first day tested the effect of saline and the second day, the effect of HDV (with 5-HT) on fasting plasma glucose levels. The protocol required that a baseline plasma glucose be obtained and followed by a 1.0 ml subcutaneous injection of saline (day 1) or HDV/5-HT (day 2). One hour later a second blood sample was obtained for a post-treatment plasma glucose. The post-treatment glucose was compared to the baseline plasma glucose values. The saline treatment (control) experiment resulted in an increased plasma glucose compared to its baseline values. However, the HDV/5-HT treatment resulted in a statistically significant ($p<0.01$) reduction in fasting plasma glucose.

The conclusions based on this data are:
1. Control saline injections in fasting dogs produced a slight (stastically insignificant) increase in the fasting plasma glucose.
2. HDV/5-HT injections produced a statistically significant ($p<0.01$ by students' t test) *reduction* of the fasting plasma glucose.

The second conclusion, namely the administration of the HDV-5HT and the resultant reduction in fasting plasma glucose is quite significant. Bearing in mind that the purpose for the foregoing test is to establish conclusively that the HDV delivers pharmacologic agents to the liver. Therefore, this invention, having first established the function in serotonin in programming the liver to uptake glucose, and then administering the serotonin in the HDV with the resultant reduction in glucose, establishes beyond any reasonable doubt that the HDV has been taken into the liver and has caused the function expected of Serotonin of ceasing glucose output and beginning glucose uptake. Following the initial in vivo testing of four dogs as listed above, addition tests on animals have been undertaken using four different programs. These four separate programs are outlined below and then summarized.

Hereafter is a description of four supplemental experiments which document the versatility of the HDV system. In the original tests above, experimental data for the hepatocyte delivery of serotonin are included. This system utilized the connector, bridge and target complex. That original study utilized the subcutaneous route of administration. The features of the original experiment and the four supplement experiments are summarized in Table I. The important variables are:

| | SUPPLEMENTAL EXPERIMENTS | | | | |
|---|---|---|---|---|---|
| | Experiment described in original experiments | 1 | 2 | 3 | 4 |
| Connector | 2,6 diisopropyl phenyl carbamoyl methyl imino diacetic acid | Same | Same | Same | Same |
| Bridge | Chromium | Chromium | Chromium | Chromium | Chromium |
| Target | 2,6 diisopropyl phenyl carbamoyl methyl imino diacetic acid | Same | Same | Same | Biliverdin |
| Hormone | Serotonin | Insulin | Growth hormone | Serotonin | Serotonin |
| Route of administration | Subcutaneous | Intravenous | Subcutaneous | Intraduodenal | Intravenous |
| Fraction of dose of hormone for effect | 1/100th | 1/200th | 1/7th to 1/50th | 1/300th | 1/100th |

1. Target molecule.

The original experiment and the first three supplemental experiments used the target molecule disclosed hereinabove. Supplemental experiment 4 used biliverdin. The differences between these two materials are very significant. The first, N-(2,6-diisopropyl phenyl carbamoyl methyl)imino diacetic acid is a synthetic material. Biliverdin is a naturally-occurring metabolite in the body that is used to form bile. Since serotonin HDV worked with both target molecules, it is established that the hepatobiliary receptor is an effective target mechanism. There is no known reference in the medical literature where a naturally-occurring metabolite, such as biliverdin, has been shown to carry and then render effective a pharmacologic cargo.

2. Different hormones.

The original experiment used serotonin as its pharmacologic cargo. The liver's response was a conversion of hepatic glucose output to uptake in selectively denervated animals. The supplemental experiments use growth hormone and insulin, as well as serotonin. All three hormones were efficacious when delivered by HDV. The serotonin was effective with both target molecules. It is also very important to recognize the superpotency conveyed to the hormones by the HDV system. Only a small fraction of the usual dose of the hormone that is required for a response is necessary for the HDV system.

3. Different routes of administration.

The HDV system is capable of delivering drugs and hormones by the three major routes of administration: Subcutaneous injection, intravenous (or arterial) infusion, and intraduodenal (oral). In the matter of the intraduodenal administration, it should be understood that the important feat to be accomplished is the transfer of the HDV from intestinal lumen through the intestinal tissues into the blood. This has been accomplished as evidenced by the pharmacologic response. The further development of the HDV to an oral dose form is expected to be rather routine by those experienced in the art and science of dose formulations.

As a result of these data, it has been experimentally shown that the hepatobiliary receptor is used to target the HDV and that molecules, synthetic or natural metabolites, which appear in some form in the bile, are suitable target molecules for this invention. Also, HDV is not selective for the carrying of one hormone, but it is a generic carrier of all drugs and hormones to hepatocytes. Furthermore, the HDV is a delivery system usable for the administering of drugs and hormones via the gastrointestinal tract (oral or rectal) and the HDV can also be used parenterally (subcutaneously, intravenously, intra-arterially, etc.).

Heretofore in this disclosure, the connector or bridge has not been varied. The critical variables are: (1) broad specificity of target molecules; (2) the ability of HDV to be administered both orally and parenterally; (3) the ability of HDV to carry different kinds of hormones; and (4) the superpotency of the drugs and hormones. Now that these critical points are experimentally demonstrated, the connector and bridge may be varied. However, it must be apparent to anyone with even a modest chemistry background that the target molecule needs to be attached to the surface of the vesicle. Once the chemical natures of the vesicle membrane and the target molecule are known it is possible to construct a multitude of workable connectors and bridges. The main requirements for connectors are to be lipophilic and insertable into the membrane and to have a compatible reactive group, such as $$R-\overset{\overset{O}{|}}{C}=O, \text{ or } R-\overset{\overset{H}{|}}{N}-, \text{ or } R-S-,$$

which can be coupled either directly to the target molecule or indirectly to the target molecule by a bridge molecule. Examples of bridges are given above.

SUPPLEMENTAL EXPERIMENT 1

HDV Insulin (HDVI): Intravenous

Connector: N-(2,6-diisopropyl phenyl carbamoyl methyl)imino diacetic acid

Bridge: Chromium

Target: N-(2,6-diisopropyl phenyl carbamoyl methyl-)imino diacetic acid

Hormone: Insulin

Route of administration: Intravenous

The purpose of this experiment was to demonstrate the efficacy of HDV Insulin, constructed with the above materials, in an insulin-deficient (diabetic) dog. The response of HDV Insulin to be measured was the conversion of hepatic glucose output to uptake by measuring the glucose (Beckman Glucose Analyzer) levels of simultaneously obtained portal and hepatic vein blood. Diabetes had been induced by the method of Black, (Am. J. Pathol. Vol 98, No. 2, pg 295-305, 1980) and sampling was done via portal and hepatic vein catheters acutely placed under general anesthesia. The dog had been fasted from food for twenty-four hours and taken off of exogenously-administered insulin for forty-eight hours.

The state of hepatic glucose output occurs when the hepatic vein glucose level (in mg%) exceeds the portal vein glucose level. Hepatic glucose uptake is the reverse.

The data for the experiment are found in the graph of FIG. 4. At "0" minutes the dog is in glucose output, and this output is maintained through the "23" and "35" minute samples, even though glucose is infused via a mesenteric vein at a rate of 0.5 g/kg body weight/hour. An intact (non-diabetic) animal would have immediately converted to glucose uptake. This dog's diabetic state is confirmed by its' not converting to glucose uptake at these times.

Following the "35" minutes sampling, HDV Insulin was infused via the left external jugular vein at a rate of 0.03 mU/kg/minute. The dog's conversion to hepatic glucose uptake is dramatically seen at 48, 55, 68 and 80 minutes, even though the HDVI infusion ceased at 60 minutes. The minimum infusion rate for insulin alone is 6.25 mU/kg/minute. Thus, this effective dose of HDVI was 1/200th of the regular insulin dose, documenting the superpotency of the HDVI in a diabetic dog by intravenous infusion.

SUPPLEMENTAL EXPERIMENT 2

HDV Growth Hormone (HDV-GH): Subcutaneous

Connector: N-(2,6-diisopropyl phenyl carbamoyl methyl)imino diacetic acid

Bridge: Chromium

Target: N-(2,6-diisopropyl phenyl carbamoyl methyl-)imino diacetic acid

Hormone: Growth Hormone

Route of administration: Subcutaneous

The purpose of this experiment was to demonstrate the efficacy of HDVGH, constructed with the above materials, in stimulating growth in hypophysectomized rats. The HDVGH was administered to rats daily by subcutaneous injection. The control rats required 10 ugGH per day (also given subcutaneously) to maintain normal growth of 1 g weight gain per day. The HDVGH treated rats attained normal growth rates with dosages of HDVGH of 0.15 to 1.5 ug per day. Thus, the HDVGH required only 1/7th to 1/50th of the regular dose of growth hormone. The HDVGH was superpotent and was efficacious when given by subcutaneous injection.

SUPPLEMENTAL EXPERIMENT 3

HDV Serotonin: Intraduodenal (Oral)

Connector: N-(2,6-diisopropyl phenyl carbamoyl methyl)imino diacetic acid

Bridge: Chromium

Target: N-(2,6-diisopropyl phenyl carbamoyl methyl-)imino diacetic acid

Hormone: Serotonin

Route of administration: Intraduodenal injection (oral)

The purpose of this experiment was to demonstrate the efficacy of HDV Serotonin, constructed with the above materials, in a selectively denervated dog that was not insulin-deficient, but in a diabetic-like state. In this model, the response of the HDV Serotonin was the conversion of hepatic glucose output to uptake. This conversion was determined by measuring the glucose levels (Beckman Glucose Analyzer) in simultaneously obtained blood samples from the portal and hepatic veins. Sampling was by means of sampling catheters acutely placed under general anesthesia.

The state of hepatic glucose output occur when the level of glucose (mg %) in the hepatic vein exceeds that of the portal vein. Hepatic glucose uptake is the reverse situation.

Data for the experiment are found in the graph of FIG. 5. At "0" minutes, during the control period, the animal is in a state of hepatic glucose output. Because of the selective denervation, the animal stays in output (at 20 and 55 minutes), even though glucose is being infused at a rate of 0.5 g/kg body weight/hour via a mesenteric vein.

The HDV Serotonin is injected into the duodenum (0.8 ml containing 3 ug serotonin/kg) at 60 minutes. At 80 and 100 minutes, the HDV Serotonin has converted the hepatic glucose output to uptake.

The conclusions are: (1) HDV Serotonin can cross from the lumen of the intestine into the blood and deliver HDV Serotonin to the hepatocyte where the serotonin is released and can carry out its pharmacologic function, and (2) HDV Serotonin is superpotent. The single intraduodenal injection of serotonin (3 ug/kg) produced a pharmacologic effect that would have required an intraporal infusion of 10–30 ug/kg body weight/minute for thirty minutes (total infused dose of serotonin per kg body weight). The intraduodenal dose was 1/300th of the necessary intraportal dose of free hormone.

SUPPLEMENTAL EXPERIMENT 4

HDV Serotonin: Intravenous
  Connector: N-2,6 diisopropyl phenyl carbamoyl methyl imino diacetic acid
  Bridge: Chromium
  Target: Biliverdin
  Hormone: Serotonin
  Route of administration: Intravenous The purpose of this experiment was to demonstrate the efficacy of HDV Serotonin, constructed with the above materials, in a selectively denervated dog. This dog, when infused with glucose, has portal vein glucose values (mg % measured with a Beckman Glucose Analyzer) that are less than hepatic vein glucose, indicating a hep hepatic glucose output. This is clearly seen in the data presented in the of FIG. 6. The dog is in a state of glucose output for time 15, 30 and 40 minutes. The HDV Serotonin was then infused at a rate of 0.3 ug/kg body weight/minute, along with the glucose. The hepatic glucose output promptly converted to uptake and was maintained even 30 minutes after discontinuing the HDV Serotonin infusion.

Figure 6:
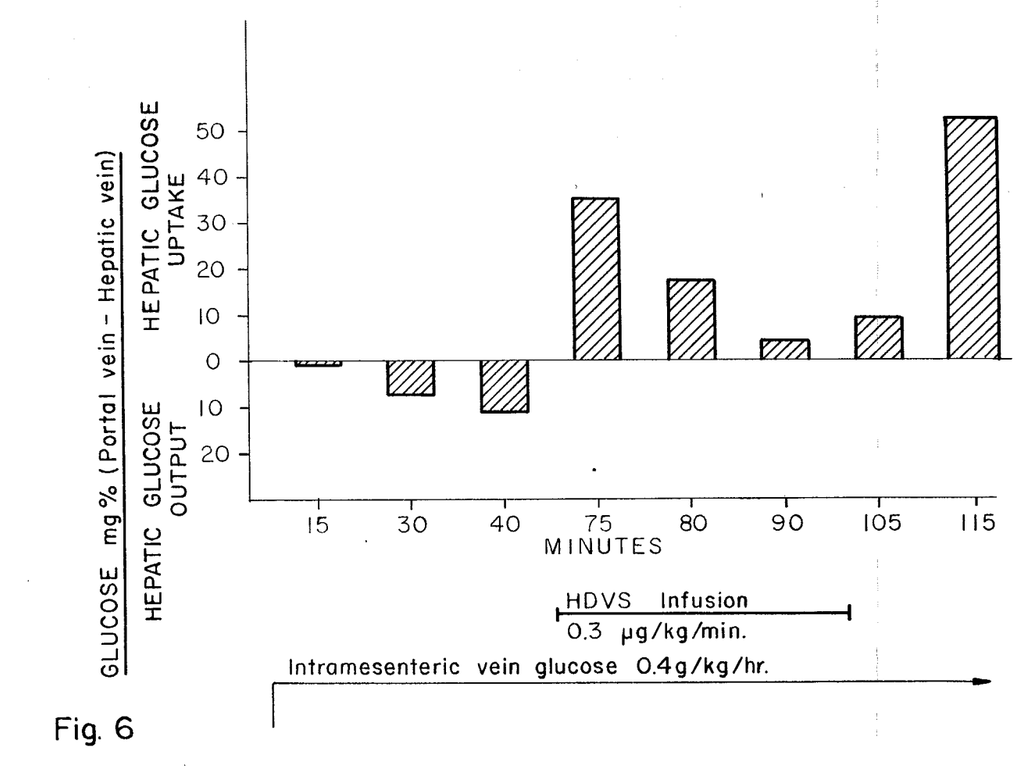
FIG. 6 is a graph comparison of the effect of correcting the lack of control serotoine on diabetic animals via intravenous injection.

This experiment demonstrates the efficacy of a different hepatobiliary target molecule, biliverdin. Its structure is markedly different from the N-2,6 diisopropyl phenyl carbamoyl imino diacetic acid used in the other experiments. The experiment also shows the typical HDV superpotency. In this experiment the HDV Serotonin was infused at a rate of 0.3 ug/kg/minute. The rate of free serotonin infusion required is 30 ug/kg/minute. The superpotency in this case is 100-fold.

The following appendix sets out a class of hepatobiliary imaging agents which has been compiled to illustrate many possible targeting agents to serve this invention. There are 86 examples. These have all been compiled by a consultant biochemist using the guide criteria that the target be a recognized hepatobiliary agent, and that a person of ordinary skill as a biochemist would be able to follow the foregoing teaching to use these materials successfully as a hepatobiliary target for a lipid vesicle.

APPENDIX

Substituted iminodiacetate (IDA) Complexes

N-(2,6-diisopropylphenyl carbamoyl methyl)iminodiacetic acid (DISIDA) (Hepatolite)

N-(2,6-diethylphenyl carbamoyl methyl)iminodiacetic acid (DIDA)

N-(2,6-dimethylphenyl carbamoyl methyl)iminodiacetic acid (HIDA)

N-(4-isopropylphenyl carbamoyl methyl)iminodiacetic acid (PIPIDA)

N-(4-butylphenyl carbamoylmethyl)iminodiacetic acid (BIDA)

N-(2,3-dimethylphenyl carbamoyl methyl)iminodiacetic acid 2,4

2,5

3,4

3,5

N-(3-butylphenyl carbamoyl methyl)iminodiacetic acid (metabutyl)
N-(2-butylphenyl carbamoyl methyl)iminodiacetic acid (orthobutyl)
N-(4-tertiary butylphenyl carbamoyl methyl)iminodiacetic acid (paratertiary butyl)
N-(3-butoxyphenyl carbamoyl methyl)iminodiacetic acid (meta butoxy)
N-(2-hexyloxyphenyl carbamoyl methyl)iminodiacetic acid (ortho hexyloxy)
N-(4-hexyloxyphenyl carbamoyl methyl)iminodiacetic acid (para hexyloxy)
Azo substituted iminodiacetic acid
iminodicarboxymethyl-2-naphthyl ketone
phthalein complexone
N-(5, pregnene-3-β-ol-2-oyl carbamoyl methyl-)iminodiacetic acid
3α: 7α: 12α: trihydroxy-24-norchol anyl-23-iminodiacetic acid
N-(3-bromo-2,4,6-trimethylphenylcarbamoyl methyl-)iminodiacetic acid
Benzimidazol methyl iminodiacetic acid N-(3-cyano-4,5-dimethyl-2-pyrryl carbamoyl methyl-)imino diacetic acid N-(3-cyano-4-methyl-5-benzyl-2-pyrryl carbamoyl methyl)iminodiacetic acid
Other Derivatives of N-(3-cyano-4-methyl-2-pyrryl carbamoyl methyl)iminodiacetic acid

| R₁ | R₂ |
|---|---|
| H | iso-C₄H₉ |
| H | CH₂CH₂SCH₃ |
| H | CH₂C₆H₄—p-OH |
| CH₃ | CH₃ |
| CH₃ | iso-C₄H₉ |
| CH₃ | CH₂CH₂SCH₃ |
| CH₃ | C₆H₅ |
| CH₃ | CH₂C₆H₅ |
| CH₃ | CH₂C₆H₄—p-OCH₃ | ethylenediamine-N,N-bis(-2-hydroxy-5-bromophenyl-)acetate
N'acyl and N'sulfonyl ethylene diamine-N,N diacetic acid
N'substituted derivatives of ethylene diamine-N,N-diacetic acid (EDDA)

EDDA
N'—acetyl EDDA

N'—benzoyl EDDA

N'—(p-toluenesulfonyl)EDDA

-continued

N'—(p-t-butylbenzoyl)EDDA

N'—(benzenesulfonyl)EDDA

N'—(p-chlorobenzenesulfonyl)EDDA

N'—(p-ethylbenzenesulfonyl)EDDA

N'—(p-n-propylbenzenesulfonyl)EDDA
N'—(naphthalene-2-sulfonyl)EDDA

N'—(2,5-dimethylbenzenesulfonyl)(EDDA)

N—(2-acetylnaphthyl)-iminodiacetic acid(NAIDA)

-continued

N—(2-naphthylmethyl)-iminodiacetic acid(NMIDA)

Hepatobiliary Dyes rose bengal
congo red
bromosulphthalein
bromophenol blue
phenolphthalein
toluidine blue
indocyanine green Hepatobiliary Contrast Agents iodipamide
ioglycamic acid—(Biligram)

Bile Salts bilirubin
cholyglycyliodohistamine
thyroxineglucuronide

Hepatobiliary Thiol Complexes penicillamine
β-mercaptoisobutyric acid
dihydrothioctic acid
6-mercaptopurine
kethoxal-bis(thiosemicarbazone)

Hepatobiliary Amine Complexes

1-hydrazinophthalazine(hydralazine)sulfonyl urea

Hepatobiliary Amino Acid Schiff Base Complexes pyridoxylidene glutamate
pyridoxylidene isoleucine
pyridoxylidene phenylalanine
pyridoxylidene tryptophan
pyridoxylidene 5-methyl tryptophan
additional pyridoxylidene aminates
3-hydroxy-4-formyl-pyridene glutamic acid Miscellaneous Hepatobiliary Complexes tetracycline 7-carboxy-β-hydroxyquinoline
phenolphthalexon eosin verograffin

What is claimed is:

1. A composition of matter for internal administration in the therapeutic treatment of a warm-blooded animal comprising:
    a first component which is a drug or diagnostic agent, said first component being encapsulated in or associated with;
    a second component which comprises lipid membrane structures in the form of vesicles or liposomes; and
    a third component which is a molecule having a fatty substituent attached to the vesicle wall and a target substituent selected from the class consisting of those chemicals which are classed biologically as biliary attracted chemicals.

2. A composition of matter as defined in claim 1 wherein the third component target substituent is a substituted iminodiacetate complex.

3. A composition of matter as defined in claim 1 wherein the third component is two substantially identical substituents joined by a bridge molecule.

4. A composition of matter as defined in claim 1 wherein the third component is two substituted iminodiacetate complex molecules joined by a bridge molecule.

5. The method of preparing a composition of matter for delivering a dose of hepatic therapeutic chemical, comprising incorporating said chemical with a lipid vesicle and connecting a chemical target molecule to the vesicle, said target molecule having preferential affinity for the hepatobiliary receptors.

6. A composition of matter for internal administration in the delivery of an effective dose of a chemical to the liver of a warm-blooded animal, comprising:
    a lipid vesicle defined by bipolar wall and containing a pharmacological cargo intended for internal utilization by the liver; and
    a compound consisting of a lipophilic substituent held in the wall of the vesicle and joined by a connector molecule to a target substituent selected from the class consisting of those chemicals which are classed biologically as biliary attracted.

7. A composition of matter for therapeutic treatment of a warm-blooded animal, comprising:
    a composite structure of a lipid vesicle, and a target moiety;
    said target moiety having a physical structure of a fatty substituent attached to the vesicle wall and a target substituent oriented in three-dimensional space extended away from the membrane surface;
    said target substituent selected from the class consisting of those chemicals which are classed biologically as having a high affinity for hepatobiliary receptors.

* * * * *